US008388942B2

(12) United States Patent
Wolfe et al.

(10) Patent No.: US 8,388,942 B2
(45) Date of Patent: Mar. 5, 2013

(54) METHODS OF INTERFERON-β PURIFICATION AND RECOVERY

(75) Inventors: Sidney N Wolfe, Lafayette, CA (US);
Bret A Shirley, Waltham, MA (US);
Susan Babuka, Oakland, CA (US);
Dennis Fordham, Richmond, CA (US);
Irina Esikova, Fremont, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 628 days.

(21) Appl. No.: 12/150,530

(22) Filed: Apr. 29, 2008

(65) Prior Publication Data

US 2009/0123424 A1    May 14, 2009

Related U.S. Application Data

(60) Continuation of application No. 10/750,076, filed on Dec. 31, 2003, now abandoned, which is a division of application No. 10/035,420, filed on Oct. 25, 2001, now Pat. No. 7,544,354.

(60) Provisional application No. 60/330,375, filed on Oct. 18, 2001, provisional application No. 60/282,607, filed on Apr. 9, 2001, provisional application No. 60/243,965, filed on Oct. 27, 2000.

(51) Int. Cl.
*A61K 38/21* (2006.01)
*C07K 14/565* (2006.01)

(52) U.S. Cl. ........................ 424/85.6; 530/351
(58) Field of Classification Search .................. None
See application file for complete search history.

(56) References Cited

U.S. PATENT DOCUMENTS

| | | | |
|---|---|---|---|
| 4,462,940 A | 7/1984 | Hanisch et al. | |
| 4,816,440 A | 3/1989 | Thomson | |
| 4,894,330 A | 1/1990 | Hershenson et al. | |
| 4,931,543 A | 6/1990 | Halenbeck et al. | |
| 4,992,271 A | 2/1991 | Fernandes et al. | |
| 5,162,507 A | 11/1992 | Wolfe et al. | |
| 5,643,566 A | 7/1997 | Hanisch et al. | |
| 5,702,699 A | 12/1997 | Hanisch et al. | |
| 5,814,485 A | 9/1998 | Dorin et al. | |
| 2003/0190307 A1* | 10/2003 | DiBiase et al. | 424/85.6 |

FOREIGN PATENT DOCUMENTS

| | | |
|---|---|---|
| EP | 0 217 645 | 4/1987 |
| EP | 0 270 799 | 6/1988 |
| EP | 0 360 937 | 4/1990 |
| EP | 0 215 658 | 6/1994 |
| KR | 9306706 | 7/1993 |
| WO | 95/31479 | 11/1995 |
| WO | 98/27211 | 6/1998 |
| WO | 02/080976 | 10/2002 |

OTHER PUBLICATIONS

Ahn, J., et al., "Investigation of Refolding Condition for *Pseudomonas fluorescens* Lipase by Response Surface Methodology", J. Biotechnol., 1997, pp. 151-160, vol. 54(3).

Bam, N., et al., "Molten Globule Intermediate of Recombinant Human Growth Hormone" Stabilization with Surfactants, Biotechnol. Prog., 1996, pp. 801-809, vol. 12(6).
Carpenter, J., and J.H. Crowe, "The Mechanism of Cryoprotection of Proteins by Solutes", Cryobiology, 1988, pp. 244-255, vol. 25(3).
Charman, S., et al., "Techniques for Assessing the Effects of Pharmaceutical Excipients on the Aggregation of Porcine Growth Hormone", Pharm. Res., 1993, pp. 954-962, vol. 10(7).
Cleland, J., et al., "Polyethylene Glycol Enhanced Protein Refolding", Biotechnology, 1992, pp. 1013-1019, vol. 10(9).
Daugherty, D., et al., "Artificial Chaperone-Assisted Refolding of Citrate Synthase", J. Biol. Chem., 1998, pp. 33961-33971, vol. 273(51).
Dryden, D., and M.P. Weit, Evidence for an Acid-Induced Molten-Globule State in Interleukin-2; A Fluorenscence and Circular Dichroism Study:, Bioichim. biophys., Acta, 1991, pp. 94-100, vol. 1078(1).
Edy, V., et al., "Stabilisation of Mouse and Human Interferons by Acid pH Against Inactivation Due to Shaking and Guanidine Hydrochloride", Proc. Soc. Exp. Biol. Med., 1974, pp. 249-253, vol. 146(1).
Edy, V., et al., "Stable and Unstable Forms of Human Fibroblst Interfereon", Infect. Immun., 1977, pp. 445-448, vol. 16(2).
Gauthier, M., and P.A. Patson, "Reactivation of C1-Inhibitor Polymers by Denaturation and Gel-Filtration Chromatography", Anal. Biochem., 1997, pp. 228-233, vol., 248(2).
Houry, W., et al., "The Nature of the Initial Step in the Conformational Folding of Disulphide-Intact Ribonuclease A", nat. Struct. Biol., 1995, pp. 495-503, vol. 2(6).
Jariwalla, R., et al., "The Reactivation of Human Interferons by Guanidine Thiocyanate", Experientia, 1980, pp. 1390-1391, vol. 36(12).
Kendrick, B., et al., "Quantitation of the Area of Overlap Between Secon-Derivative Amide I Infrared Spectra to Determine the Structural Similarity of a Protein in Different States", J. Pharm. Sci., 1996, pp. 155-158, vol. 85(2).
Lee, J.K., et al., "Purificatin of Human Interferon-62 from Recombinant *E. coli*", Korean Biochemical Journal, 1990, pp. 166-171, vol. 23(2).

(Continued)

*Primary Examiner* — Robert Landsman
*Assistant Examiner* — Bruce D Hissong
(74) *Attorney, Agent, or Firm* — Andrew K. Holmes; Cozette M. McAvoy (57) ABSTRACT

Improved methods for purification and recovery of interferon-beta (IFN-β) and compositions comprising substantially monomeric IFN-β are provided. In one purification method, substantially purified IFN-β or variant thereof is precipitated and then dissolved in a guanidine hydrochloride (HCl) solution. Renaturation of the protein occurs by dilution with a suitable buffer. A similar purification method absent the precipitation step is also provided. Following renaturation of the IFN-β, residual guanidine HCl is removed by diafiltration or dialysis with a pharmaceutically acceptable buffer to prepare pharmaceutical compositions comprising substantially monomeric IFN-β.

35 Claims, 3 Drawing Sheets

OTHER PUBLICATIONS

Muzammil, S., et al., "Molten Globule-Like State of Human Serum Albumin at low pH", Eur. J. Biochem, 1999, pp. 26-32, vol. 266(1).

Pepinsky, R.B., "Selective Precipitation of Proteins from Guanidine Hydrochloride-Containing Solutions with Ethanol", Analytical Biochemistry, 1991, pp. 177-181, vol. 195.

Rozema, D., and S.H. Gellman, "Artificial Chaperone-Assisted Refolding of Denatured-Reduced Lysozyme: Modulation of the Competition Between Renaturation and Aggregation", Biochemistry, 1996, pp. 15760-15771, vol. 35(49).

Rozema, D., and S.H. Gellman, "Artificial Chaperone-Assisted Refolding of Carbonic Anhydrase B", J. Biol. Chem., 1996, pp. 3478-3487, vol. 271(7).

Russell-Harde, E., et al., "The Use of Zwittergent 3-14 in the Purification of Recombinant Human Interferon-β Ser17(Betaseron)", Journal of Interferon and Cytokine Research, 1995, pp. 31-37, vol. 15(1).

Todhunter, R., et al., "Structure of Equine Type I and Type II Collagens", Am. J. Vet. Res., 1994, pp. 425-431, vol. 55(3).

Van Oss, C.J., On the Mechanism of the Cold Ethanol Precipitaion Method of Plasma Protein Fractionation, Journal of Protein Chemistry, 1989, pp. 661-668, vol. 8(5).

Weir, M., et al., "Micropreparative Purification of Recombinant Human Interleukin-2", J. Chromatogr., 1987, pp. 209-215. vol. 396.

Xie, Y. and D.B. Wetlaufer, "Control of Aggregation in Protein Refolding" The Temperature-Leap Tactic, Protein Sci., 1996, pp. 517-523, vol. 5(3).

Mickle JE el al., "Genotype-phenotype relationships in cyctic fibrosis", 2000, Med. Clin. North Am., vol. 84, No. 3, pp. 597-607.

Arora D et al., "Method for Increasing the yield of Properly Folded Recombinant Human Gamma Interferon from Inclusion Bodies", J. Biotech., 1996, vol. 52, pp. 127-133.

* cited by examiner

Figure 1
Dilution of Guanidine HCl (8 M) IFN (~10mg/ml) to 0.2 M Guanidine in Various Buffers Sizing HPLC Chromatograms

Figure 2

The Effect of Salt and pH on the Recovery of IFN From 0.4 M Guanidine HCl, 10 mM NaPO$_4$, pH 7.0 Buffer Figure 3
Effect of Tween 80 (% concentration) on the Aggregation of Renatured IFN

SEQUENCE LISTING

```
<160> NUMBER OF SEQ ID NOS: 2

<210> SEQ ID NO 1
<211> LENGTH: 166
<212> TYPE: PRT
<213> ORGANISM: Homo sapiens

<400> SEQUENCE: 1

Met Ser Tyr Asn Leu Leu Gly Phe Leu Gln Arg Ser Ser Asn Phe Gln
 1               5                  10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
```

```
                50                    55                    60
Asn Ile Phe Ala Leu Phe Arg Gln Asp Ser Ser Ser Thr Gly Trp Asn
 65                      70                      75                      80

Glu Thr Ile Val Glu Asn Leu Leu Ala Asn Val Tyr His Gln Ile Asn
                         85                      90                      95

His Leu Lys Thr Val Leu Glu Glu Lys Leu Glu Lys Glu Asp Phe Thr
                        100                     105                     110

Arg Gly Lys Leu Met Ser Ser Leu His Leu Lys Arg Tyr Tyr Gly Arg
                        115                     120                     125

Ile Leu His Tyr Leu Lys Ala Lys Glu Tyr Ser His Cys Ala Trp Thr
                        130                     135                     140

Ile Val Arg Val Glu Ile Leu Arg Asn Phe Tyr Phe Ile Asn Arg Leu
145                     150                     155                     160

Thr Gly Tyr Leu Arg Asn
                        165

<210> SEQ ID NO 2
<211> LENGTH: 166
<212> TYPE: PRT
<213> ORGANISM: Artificial Sequence
<220> FEATURE:
<223> OTHER INFORMATION: C17S mutein of mature human IFN-beta

<400> SEQUENCE: 2

Met Ser Tyr Asn Leu Leu Gly Phe Leu Gln Arg Ser Ser Asn Phe Gln
  1                       5                      10                      15

Ser Gln Lys Leu Leu Trp Gln Leu Asn Gly Arg Leu Glu Tyr Cys Leu
                         20                      25                      30

Lys Asp Arg Met Asn Phe Asp Ile Pro Glu Glu Ile Lys Gln Leu Gln
                         35                      40                      45

Gln Phe Gln Lys Glu Asp Ala Ala Leu Thr Ile Tyr Glu Met Leu Gln
                         50                      55                      60

Asn Ile Phe Ala Leu Phe Arg Gln Asp Ser Ser Ser Thr Gly Trp Asn
 65                      70                      75                      80

Glu Thr Ile Val Glu Asn Leu Leu Ala Asn Val Tyr His Gln Ile Asn
                         85                      90                      95

His Leu Lys Thr Val Leu Glu Glu Lys Leu Glu Lys Glu Asp Phe Thr
                        100                     105                     110

Arg Gly Lys Leu Met Ser Ser Leu His Leu Lys Arg Tyr Tyr Gly Arg
                        115                     120                     125

Ile Leu His Tyr Leu Lys Ala Lys Glu Tyr Ser His Cys Ala Trp Thr
                        130                     135                     140

Ile Val Arg Val Glu Ile Leu Arg Asn Phe Tyr Phe Ile Asn Arg Leu
145                     150                     155                     160

Thr Gly Tyr Leu Arg Asn
                        165
```

METHODS OF INTERFERON-β PURIFICATION AND RECOVERY

CROSS-REFERENCE TO RELATED APPLICATIONS

This is a continuation of application Ser. No. 10/750,076 filed on Dec. 31, 2003, which is a divisional of application Ser. No. 10/035,420 filed on Oct. 25, 2001, which claims benefit of U.S. Provisional Application 60/243,965 filed on Oct. 27, 2000, U.S. Provisional Application 60/282,607 filed on Apr. 9, 2001, and U.S. Provisional Application 60/330,375 filed on Oct. 18, 2001, the entire disclosures of which are hereby incorporated by reference.

This application claims the benefit of U.S. application Ser. No. 10/035,420, filed Oct. 25, 2003, and U.S. Provisional Application Ser. No. 60/330,375, filed Oct. 18, 2001, U.S. Provisional Application Ser. No. 60/282,607, filed Apr. 9, 2001, and U.S. Provisional Application Ser. No. 60/243,965, filed Oct. 27, 2000, each of which is herein incorporated by reference in its entirety.

FIELD OF THE INVENTION

This invention relates to the field of biochemical engineering. More particularly, the invention concerns an improved biochemical recovery process in which recombinant interferon-beta can be refolded and recovered in substantially pure and monomeric form. This composition can be used in pharmaceutical formulations.

BACKGROUND OF THE INVENTION

Naturally occurring interferons are species-specific proteins produced by various cells upon induction with viruses, double-stranded RNAs, other polynucleotides, antigens, and mitogens. Interferons exhibit multiple biological activities, including antiviral, antiproliferative, immunomodulatory, and anticellular activities. Investigation of these activities has led to the identification and characterization of at least three distinct types of human interferons, which are reported to be different proteins encoded by distinct structural genes. Interferons, which are often glycoproteins, were originally classified based on their cell source and later reclassified as alpha, beta ("β"), and gamma.

Interferon-beta ("IFN-β") is produced by fibroblasts and epithelial cells. Native interferon-beta was produced by superinducing human fibroblast cultures with polyriboinosinic acid and polyribocytidylic acid and isolating and purifying the interferon(s) thus produced by chromatographic and electrophoretic techniques. The expense and difficulty of purifying interferons in this way precluded extensive clinical testing and evaluation of interferons' therapeutic value. Isolation of interferons from natural sources remains relatively difficult and expensive.

More recently, several of the human interferon genes have been cloned using recombinant DNA ("rDNA") technology and have been expressed in *E. coli* (Nagola et al. (1980) *Nature* 284:316; Goeddel et al. (1980) *Nature* 287:411; Yelverton et al. (1981) *Nucleic Acids Res.* 9:731; Streuli et al. (1981) *Proc. Natl. Acad. Sci. USA* 78:2848). Proteins or polypeptides that exhibit native interferon-beta-like properties may also be produced with rDNA technology by extracting poly-A-rich 12S messenger RNA from virally induced human cells, synthesizing double-stranded cDNA using the mRNA as a template, introducing the cDNA into an appropriate cloning vector, transforming suitable microorganisms with the vector, harvesting the microorganisms, and extracting the interferon-beta therefrom. See, for example, European Patent Application Nos. 28033 (published May 6, 1981); 32134 (published Jul. 15, 1981); and 34307 (published Aug. 26, 1981), which describe various methods for the production of interferon-beta employing rDNA techniques. The expressed proteins or polypeptides from recombinant DNA clones have been purified, tested, and found to exhibit properties similar to those of native interferons. Bacterially produced interferons thus have potential therapeutic use as antiviral and antitumor agents. The production of interferons by such bacterial fermentations yields large quantities of interferon at a relatively low cost, thereby making interferon more widely available for many uses, such as clinical studies.

Interferon-beta for use in clinical studies must be of relatively high purity and substantially uncontaminated with toxic host cell constituents, cell debris, and other extraneous chemicals introduced during the extraction and purification steps. There are several methods currently available for the preparation, recovery, and purification of IFN-β.

The methods of purification and recovery of IFN-β disclosed in U.S. Pat. Nos. 4,462,940 and 5,702,699 and similar methods produce a pure form of IFN-β that tends to form aggregates in the absence of strong solubilizers, e.g., sodium dodecyl sulfate ("SDS"). In addition, such methods (1) expose the protein to high pH conditions that may adversely affect the protein's biological properties, and (2) result in compositions containing residual amounts of SDS used to solubilize the protein during purification.

Therefore, there is a need for an improved recovery and purification process in which the IFN-β is not subjected to high alkalinity, the formulation is free or virtually free of SDS, and the protein is soluble at a pH suitable for parenteral administration. It is an object of the present invention to provide a pharmaceutically acceptable sample of IFN-β that is of relatively high purity and easily refolded during the purification and recovery process.

SUMMARY OF THE INVENTION

Improved methods useful in the preparation of pharmaceutical formulations of IFN-β are provided. The methods provide monomeric, liquid pharmaceutical compositions comprising IFN-β. The methods include conditions that enhance refolding of the protein during the recovery process.

To achieve the foregoing and other objects and in accordance with the purpose of the present invention as embodied and broadly described herein, the present invention provides improved methods for the purification and recovery of IFN-β. In one embodiment, the improved method comprises preparing a solution comprising IFN-β, isolating a pool of substantially purified IFN-β from this solution, precipitating the purified IFN-β from this pool using an alcohol, and dissolving the precipitated IFN-β into guanidine hydrochloride to form a solution comprising resolubilized denatured IFN-β. This solution comprising resolubilized denatured IFN-β is then diluted into an appropriate first buffer to obtain a solution comprising resolubilized renatured IFN-β. The resulting solution is then diafiltered or dialyzed into a buffer suitable for pharmaceutical purposes. This last step removes residual guanidine hydrochloride, yielding a pharmaceutical formulation comprising substantially monomeric IFN-β suitable for parenteral administration.

In another embodiment, the improved method of purification and recovery of IFN-β comprises obtaining a sample of substantially purified IFN-β and mixing this sample with guanidine hydrochloride to form a solution comprising solubilized denatured IFN-β. This solution comprising solubilized denatured IFN-β is then diluted into an appropriate first buffer to obtain a solution comprising solubilized renatured IFN-β. The resulting solubilized renatured IFN-β solution is then diafiltered or dialyzed into a buffer suitable for pharmaceutical purposes. As noted above, this last step removes the residual guanidine hydrochloride, yielding a pharmaceutical formulation comprising substantially monomeric IFN-β suitable for parenteral administration.

Another aspect of the present invention deals with an improved process for the recovery of microbially produced IFN-β. Using the methods of the invention, it is possible to prepare IFN-β pharmaceutical formulations that are free or virtually free of SDS (less than 10 micrograms SDS per milligram of IFN-β. Another aspect of the present invention is that substances such as human serum albumin (HSA) are not necessary for a stable preparation of IFN-β when the methods of the present invention are employed. The substantially monomeric form of IFN-β may then be diluted into an aqueous buffer for use in pharmaceutical formulations. Thus, the methods find use in preparation of the pharmaceutical compositions of the invention.

DETAILED DESCRIPTION OF THE INVENTION

The present invention is directed to novel methods of preparing a substantially monomeric form of IFN-β. By "substantially monomeric" is intended that the majority of IFN-β (by weight) present in a preparation or composition is monomeric rather than aggregated. By "aggregated" is intended a physical interaction between the polypeptide molecules that results in the formation of non-covalent multimers that may remain soluble or that may precipitate out of solution. The percentage (by weight) of IFN-β that is monomeric in a substantially monomeric composition or formulation may vary from 51% or greater. The methods of the invention provide for preparation of compositions comprising substantially monomeric IFN-β that are made without the use of the traditional stabilizer HSA and which are free or virtually free of the solubilizer sodium dodecyl sulfate (SDS) (i.e., containing less that 10 micrograms SDS per-milligram of IFN-β). These compositions comprising substantially monomeric IFN-β are therefore suitable for use in pharmaceutical or therapeutic preparations. The monomeric form of the IFN-β polypeptide remains soluble, and hence is said to be "solubilized" in the pharmaceutical compositions of the present invention. The present invention thus provides HSA-free, SDS-free, IFN-β pharmaceutical compositions that comprise at least about 51% of the IFN-β in its monomeric form, as opposed to its aggregated form, preferably at least about 55%, 60%, 65%, 70%, 75%, 80%, 85%, more preferably at least about 90% or more of the IFN-β in its monomeric form.

In one embodiment, the composition comprising substantially monomeric IFN-β is prepared by precipitating substantially purified IFN-β from solution, resuspending the precipitate by dissolution in guanidine hydrochloride (HCl), removing any residual SDS by filtration where the initial IFN-β sample comprises SDS, and then renaturing the IFN-β by dilution of the resulting guanidine HCl-IFN-β solution with an appropriate buffer solution. By "substantially purified" is intended the IFN-β in the starting material is substantially or essentially free from components that normally accompany or interact with the protein as found in its naturally occurring environment, i.e., a native cell, or host cell in the case of recombinantly produced IFN-β. An IFN-β polypeptide that is substantially free of cellular material includes preparations of protein having less than about 30%, 25%, 20%, 15%, 10%, 5%, or 1% (by dry weight) of contaminating protein. When the IFN-β polypeptide or biologically active variant thereof is recombinantly produced, preferably culture medium represents less than about 30%, 25%, 20%, 15%, 10%, 5%, or 1% (by dry weight) of chemical precursors or non-protein-of-interest chemicals. Thus, "substantially purified" IFN-β for use in the methods of the present invention is said to have a purity level of at least about 70%, preferably a purity level of at least about 75%, 80%, 85%, more preferably a purity level of at least about 90% or greater as determined by SDS/PAGE analysis.

In another embodiment, the composition comprising substantially monomeric IFN-β is prepared in the absence of the precipitation step noted above. In this manner, a sample comprising substantially purified IFN-β is mixed with guanidine HCl to obtain a solution comprising solubilized denatured IFN-β; the IFN-β is then renatured by dilution of the resulting guanidine HCl-IFN-β solution with an appropriate buffer. The ramifications of these preparation steps are the basis for the compositions comprising substantially monomeric IFN-β and methods of the present invention for preparing injectable formulations comprising substantially monomeric IFN-β that are useful for IFN-β therapy directed to IFN-β-responsive diseases.

The term "IFN-beta" or "IFN-β" as used herein refers to IFN-β or variants thereof, sometimes referred to as IFN-β-like polypeptides. Thus, for example, human IFN-β variants, which may be naturally occurring (e.g., allelic variants that occur at the IFN-β locus) or recombinantly produced, have amino acid sequences that are the same as, similar to, or substantially similar to the mature native human IFN-β sequence. Fragments of IFN-β or truncated forms of IFN-β that retain their activity are also encompassed by the term "IFN-β" or "IFN-beta." These biologically active fragments or truncated forms of IFN-β are generated by removing amino acid residues from the full-length IFN-β amino acid sequence using recombinant DNA techniques well known in the art. IFN-β polypeptides may be glycosylated (IFN-β-1a) or unglycosylated (IFN-β-1b), as it has been reported in the literature that both the glycosylated and unglycosylated IFN-βs show qualitatively similar specific activities and that, therefore, the glycosyl moieties are not involved in and do not contribute to the biological activity of IFN-β. The IFN-β variants encompassed herein include muteins of the native mature IFN-β sequence shown in SEQ ID NO:1 (see, for example, U.S. Pat. No. 5,814,485, herein incorporated by reference), wherein one or more cysteine residues that are not essential to biological activity have been deliberately deleted or replaced with other amino acids to eliminate sites for either intermolecular crosslinking or incorrect intramolecular disulfide bond formation. IFN-β variants of this type include those containing a glycine, valine, alanine, leucine, isoleucine, tyrosine, phenylalanine, histidine, tryptophan, serine, threonine, or methionine substituted for the cysteine found at amino acid 17 of the mature native amino acid sequence.

Serine and threonine are the more preferred replacements because of their chemical analogy to cysteine. Serine substitutions are most preferred. See, for example, the IFN-β variant where the cysteine found at amino acid 17 of the mature native sequence is replaced with serine (SEQ ID NO:2; U.S. Pat. No. 5,814,485). Cysteine 17 may also be deleted using methods known in the art (see, for example, U.S. Pat. No. 4,518,584, herein incorporated by reference), resulting in a mature IFN-β mutein that is one amino acid shorter than the native mature IFN-β. See also, as examples, U.S. Pat. Nos. 4,530,787; 4,572,798; and 4,588,585. Thus, IFN-β variants with one or more mutations that improve, for example, their pharmaceutical utility are also encompassed by the present invention.

The skilled artisan will appreciate that additional changes can be introduced by mutation into the nucleotide sequences encoding IFN-β, thereby leading to changes in the IFN-β amino acid sequence, without altering the biological activity of the interferon. Thus, an isolated nucleic acid molecule encoding an IFN-β variant having a sequence that differs from the amino acid sequence for the native IFN-β can be created by introducing one or more nucleotide substitutions, additions, or deletions into the corresponding nucleotide sequence encoding the native IFN-β, such that one or more amino acid substitutions, additions or deletions are introduced into the encoded IFN-β. Mutations can be introduced by standard techniques, such as site-directed mutagenesis and PCR-mediated mutagenesis. Such IFN-β variants are also encompassed by the present invention.

For example, conservative amino acid substitutions may be made at one or more predicted, preferably nonessential amino acid residues. A "nonessential" amino acid residue is a residue that can be altered from the wild-type sequence of IFN-β without altering its biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Such substitutions would not be made for conserved amino acid residues, or for amino acid residues residing within a conserved motif.

Alternatively, variant IFN-β nucleotide sequences can be made by introducing mutations randomly along all or part of an IFN-β coding sequence, such as by saturation mutagenesis, and the resultant mutants can be screened for IFN-β biological activity to identify mutants that retain activity. Following mutagenesis, the encoded protein can be expressed recombinantly, and the activity of the protein can be determined using standard assay techniques described herein.

Biologically active variants of IFN-β will generally have at least 80%, more preferably about 90 to 95% or more, and most preferably about 99% amino acid sequence identity to the amino acid sequence of the reference IFN-β molecule, for example the native human-IFN-β, which serves as the basis for comparison. By "sequence identity" is intended the same amino acid residues are found within the variant polypeptide and the polypeptide molecule that serves as a reference when a specified, contiguous segment of the amino acid sequence of the variant is aligned and compared to the amino acid sequence of the reference molecule.

For purposes of optimal alignment of the two sequences for determining sequence identity, the contiguous segment of the amino acid sequence of the variant may have additional amino acid residues or deleted amino acid residues with respect to the amino acid sequence of the reference molecule. The contiguous segment used for comparison to the reference amino acid sequence will comprise at least 20 contiguous amino acid residues. Corrections for increased sequence identity associated with inclusion of gaps in the variant's amino acid sequence can be made by assigning gap penalties. Methods of sequence alignment are well known in the art.

Thus, the determination of percent identity between any two sequences can be accomplished using a mathematical algorithm. One preferred, non-limiting example of a mathematical algorithm utilized for the comparison of sequences is the algorithm of Myers and Miller (1988) *Comput. Appl. Biosci.* 4:11-7. Such an algorithm is utilized in the ALIGN program (version 2.0), which is part of the GCG alignment software package. A PAM120 weight residue table, a gap length penalty of 12, and a gap penalty of 4 can be used with the ALIGN program when comparing amino acid sequences. Another preferred, non-limiting example of a mathematical algorithm for use in comparing two sequences is the algorithm of Karlin and Altschul (1990) *Proc. Natl. Acad. Sci. USA* 90:5873-5877, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:403-410. BLAST amino acid sequence searches can be performed with the XBLAST program, score=50, wordlength=3, to obtain amino acid sequence similar to the polypeptide of interest. To obtain gapped alignments for comparison purposes, gapped BLAST can be utilized as described in Altschul et al. (1997) *Nucleic Acids Res.* 25:3389-3402. Alternatively, PSI-BLAST can be used to perform an integrated search that detects distant relationships between molecules. See Altschul et al. (1997) supra: When utilizing BLAST, gapped BLAST, or PSI-BLAST programs, the default parameters can be used. See the website for ncbi.nlm.nih.gov. Also see the ALIGN program (Dayhoff (1978) in *Atlas of Protein Sequence and Structure* 5 Suppl. 3, National Biomedical Research Foundation, Washington, D.C.) and programs in the Wisconsin Sequence Analysis Package, Version 8 (available from Genetics Computer Group, Madison, Wis.), for example, the GAP program, where default parameters of the programs are utilized.

When considering percentage of amino acid sequence identity, some amino acid residue positions may differ as a result of conservative amino acid substitutions, which do not affect properties of protein function. In these instances, percent sequence identity may be adjusted upwards to account for the similarity in conservatively substituted amino acids. Such adjustments are well known in the art. See, for example, Myers and Miller (1988) *Comput. Appl. Biosci.* 4:11-17.

Biologically active variants of IFN-β encompassed by the invention should retain IFN-β activities, particularly the ability to bind to IFN-β receptors. The biological activity of IFN-β variants can be measured by any method known in the art. Examples of such assays can be found in Fellous et al. (1982) *Proc. Natl. Acad Sci USA* 79:3082-3086; Czerniecki et al. (1984) *J. Virol.* 49(2):490-496; Mark et al. (1984) *Proc. Natl. Acad. Sci. USA* 81:5662-5666; Branca et al. (1981) *Nature* 277:221-223; Williams et al. (1979) *Nature* 282:582-586; Herberman et al. (1979) *Nature* 277:221-223; and Anderson et al. (1982) *J. Biol. Chem.* 257(19):11301-11304.

Non-limiting examples of IFN-β polypeptides and IFN-β variant polypeptides encompassed by the invention are set forth in Nagata et al. (1980) *Nature* 284:316-320; Goeddel et al. (1980) *Nature* 287:411-416; Yelverton et al. (1981) *Nucleic Acids Res.* 9:731-741; Streuli et al. (1981) *Proc. Natl. Acad. Sci. USA* 78:2848-2852; EP028033B1, and EP109748B1. See also U.S. Pat. Nos. 4,518,584; 4,569,908; 4,588,585; 4,738,844; 4,753,795; 4,769,233; 4,793,995; 4,914,033; 4,959,314; 5,545,723; and 5,814,485. These disclosures are herein incorporated by reference. These citations also provide guidance regarding residues and regions of the IFN-β polypeptide that can be altered without the loss of biological activity.

By "recombinantly produced IFN-β" is intended IFN-β that has comparable biological activity to native IFN-β and that has been prepared by recombinant DNA techniques. IFN-β can be produced by culturing a host cell transformed with an expression vector comprising a nucleotide sequence that encodes an IFN-β polypeptide. The host cell is one that can transcribe the nucleotide sequence and produce the desired protein, and can be prokaryotic (for example, *E. coli*) or eukaryotic (for example a yeast, insect, or mammalian cell). Examples of recombinant production of IFN-β are given in Mantei et al. (1982) *Nature* 297:128; Ohno et al. (1982) *Nucleic Acids Res.* 10:967; Smith et al. (1983) *Mol. Cell. Biol.* 3:2156, and U.S. Pat. Nos. 4,462,940, 5,702,699, and 5,814,485; herein incorporated by reference. See also U.S. Pat. No. 5,795,779, where IFN-β-1a is recombinantly produced in Chinese hamster ovary (CHO) cells; herein incorporated by reference. Human interferon genes have been cloned using recombinant DNA ("rDNA") technology and have been expressed in *E. coli* (Nagola et al. (1980) *Nature* 284:316; Goeddel et al. (1980) *Nature* 287:411; Yelverton et al. (1981) *Nuc. Acid Res.* 9:731; Streuli et al. (1981) *Proc. Nail Acad. Sci. U.S.A.* 78:2848). Alternatively, IFN-β can be produced by a transgenic animal or plant that has been genetically engineered to express the IFN-β protein of interest in accordance with methods known in the art.

Proteins or polypeptides that exhibit native interferon-beta-like properties may also be produced with rDNA technology by extracting poly-A-rich 12S messenger RNA from virally induced human cells, synthesizing double-stranded cDNA using the mRNA as a template, introducing the cDNA into an appropriate cloning vector, transforming suitable microorganisms with the vector, harvesting the microorganisms, and extracting the interferon-beta therefrom. See, for example, European Patent Application Nos. 28033 (published May 6, 1981); 32134 (published Jul. 15, 1981); and 34307 (published Aug. 26, 1981), which describe various methods for the production of IFN-β employing rDNA techniques.

Alternatively, IFN-β can be synthesized chemically, by any of several techniques that are known to those skilled in the peptide art. See, for example, Li et al. (1983) *Proc. Natl. Acad. Sci. USA* 80:2216-2220, Steward and Young (1984) *Solid Phase Peptide Synthesis* (Pierce Chemical Company, Rockford, Ill.), and Baraney and Merrifield (1980) *The Peptides: Analysis, Synthesis, Biology*, ed. Gross and Meinhofer, Vol. 2 (Academic Press, New York, 1980), pp. 3-254, discussing solid-phase peptide synthesis techniques; and Bodansky (1984) *Principles of peptide Synthesis* (Springer-Verlag, Berlin) and Gross and Meinhofer, eds. (1980) *The Peptides: Analysis, Synthesis, Biology*, Vol. 1 (Academic Press, New York), discussing classical solution synthesis. IFN-β can also be chemically prepared by the method of simultaneous multiple peptide synthesis. See, for example, Houghten (1984) *Proc. Natl. Acad. Sci. USA* 82:5131-5135; and U.S. Pat. No. 4,631,211.

Preparation of the compositions comprising substantially monomeric IFN-β disclosed herein is preferably carried out in accordance with one of the two improved purification methods of the present invention. The first of these purification methods comprises three basic steps: (1) precipitation of IFN-β from a solution comprising substantially purified IFN-β; (2) dissolution of the IFN-β precipitate in guanidine hydrochloride (HCl) to achieve resolubilization of the IFN-β; and (3) renaturation of the IFN-β, preferably via dilution or dialysis using an acceptable buffer. This purification method produces IFN-β that is soluble, stable, and in substantially monomeric form. The resulting composition can be formulated as a pharmaceutical composition by further diafiltration or dialysis of this composition with a pharmaceutically acceptable buffer. This final step removes residual guanidine HCl from the solution comprising renatured IFN-β and provides for a formulation having a pH that is acceptable for parenteral administration.

Using this purification method of the invention, a precipitate of IFN-β is first prepared by precipitating substantially purified IFN-β from a solution. Precipitation is accomplished by reducing the solubility of IFN-β. Reduction of IFN-β solubility and precipitation of IFN-β may be achieved with the use of an alcohol, for example an aliphatic alcohol such as ethanol. For some proteins, precipitation results from a denaturation and/or aggregation reaction that is irreversible, leading to protein inactivation, but in the case of the precipitated IFN-β of the present invention, the precipitation reaction is reversible. Thus, the soluble IFN-β recovered in the subsequent steps of this purification method retains its biological activity.

The resulting precipitate is then dissolved in guanidine HCl to obtain a solution comprising resolubilized denatured IFN-β and guanidine HCl. In those instances where the substantially purified IFN-β has been obtained using an initial purification step that includes the use of SDS as a solubilizer, the SDS remains as a precipitate following dissolution with guanidine HCl. This precipitated SDS is removed by filtration using standard filtration techniques known in the art, preferably prior to carrying out the subsequent steps of this improved purification method. The amount of guanidine HCl to be mixed with the IFN-β precipitate is an amount sufficient to solubilize the precipitated IFN-β in the resulting guanidine HCl-IFN-β solution, i.e., about 6 M to about 10 M guanidine HCl, preferably about 6 M to about 9 M, more preferably about 6M to about 8 M guanidine HCl in this resulting guanidine HCl-IFN-β solution. Though solubilized, the IFN-β in this solution is also denatured. Renaturation of the protein is accomplished by dilution of the guanidine HCl-IFN-β solution with a buffer solution, whereby a solution comprising resolubilized renatured IFN-β and residual guanidine hydrochloride is obtained. The IFN-β in this resulting solution is substantially monomeric, i.e., at least about 51% is in its monomeric form, preferably at least about 70%, 75%, 80%, 85%, more preferably at least about 90% or more is in its monomeric form as determined, for example, by sizing HPLC.

During the resolubilization and renaturation steps, guanidine HCl serves as a solubilizing agent to enhance the solubility of IFN-β. By "enhancing the solubility" of IFN-β is intended increasing the amount of IFN-β that can be dissolved in solution at about pH 3.0 to about pH 9.0 in the presence of guanidine HCl when compared to the amount of IFN-β that can be dissolved at the same pH in a solution with the same components but lacking guanidine HCl. The ability of guanidine HCl to enhance the solubility of IFN-β can be determined using methods well known in the art, including those disclosed herein.

Any suitable buffer may be used in the dilution step of this purification method of the invention to achieve renaturation of the IFN-β. Suitable buffers for use in this step include those disclosed below, such as acetate, citrate, phosphate, and Tris HCl, the choice of which will depend upon the desired pH of the resulting solution following the dilution step. When the purification method includes the precipitation step, preferably the buffer used for the dilution step has a pH of about 4.0 to about 8.0, including about 4.0, 4.5, 5.0, 5.5, 6.0, 6.5, 7.0, 7.5, and 8.0, more preferably a pH of about 5.0 to about 7.0. Following this dilution step, preferably the amount of residual guanidine HCl remaining in the resolubilized renatured IFN-β solution is about 1.6 M or less, more preferably about 0.8 M or less.

The resulting resolubilized renatured IFN-β solution comprises the IFN-β substantially in its monomeric form (i.e., greater than about 51% is monomeric). In addition, the resolubilized renatured IFN-β solution comprises a residual amount of guanidine HCl. This composition can be utilized for preparation of pharmaceutical formulations that are suitable for parenteral administration. In this manner, the residual guanidine HCl solubility enhancer can be removed from the resolubilized renatured IFN-β solution by dialysis or diafiltration of this solution with a pharmaceutically acceptable buffer. By "removal of residual guanidine HCl" is intended the pharmaceutical formulation comprising substantially monomeric IFN-β prepared using the steps of this purification method comprises guanidine HCl at a concentration of 10 mM or less, preferably 5 mM or less. Any pharmaceutically acceptable buffer can be used to make the pharmaceutical formulation so long as the IFN-β remains solubilized and substantially in its monomeric form. In one embodiment, the pharmaceutically acceptable buffer comprises arginine or sodium chloride in an amount sufficient to increase yield of the monomeric form of IFN-β as compared to the yield obtained in the absence of arginine or sodium chloride in the pharmaceutically acceptable buffer. For arginine, the amount sufficient to increase yield is about 0.2 M to about 1.0 M, preferably about 0.4 M to about 0.8 M, including about 0.4 M, 0.5 M, 0.6 M, 0.7 M, and 0.8 M. In one embodiment, the amount of arginine present in the pharmaceutically acceptable buffer is about 0.5 M. For sodium chloride, the amount sufficient to increase yield is about 0.2 M to about 1.2 M, preferably about 0.2 M to about 1.0 M, more preferably about 0.5 M to about 1.0 M. In one embodiment, the amount of sodium chloride present in the pharmaceutically acceptable buffer is about 1.0 M.

The second purification method for preparing a composition comprising substantially monomeric IFN-β is similar to the first method, but provides a means of preparing this composition without the precipitation step. This second method comprises two basic steps: (1) mixing a sample comprising substantially purified IFN-β with guanidine hydrochloride (HCl) to obtain a solution comprising solubilized denatured IFN-β; and (2) renaturation of the IFN-β, preferably via dilution using an acceptable buffer. The guanidine HCl serves as a solubility enhancing agent as noted above, and is used in amounts similar to that noted above for the first purification method. Thus, after the first step, the amount of guanidine HCl in the solution comprising solubilized denatured IFN-β is about 6 M to about 10 M guanidine HCl, preferably about 6 M to about 9 M, more preferably about 6 M to about 8 M guanidine HCl. As noted above, where the initial substantially purified IFN-β contains SDS, the SDS precipitates in this step and can be filtered from the solution using standard filtration techniques known in the art.

As in the first purification method, the IFN-β in this guanidine HCl-IFN-β solution is denatured. Renaturation is achieved by dilution using an acceptable buffer having a pH in the range of about 3.0 to about 5.0, preferably about 3.0 to about 4.0, more preferably about 3.0. Suitable buffers for this dilution step to accomplish renaturation of the IFN-β include glycine, aspartic acid, glutamic acid, and succinate, acetate, phosphate, formate, and citrate, as well as any salts thereof. Following this dilution step, preferably the amount of residual guanidine HCl remaining in the solubilized renatured IFN-β solution is about 1.6 M or less, preferably about 0.8 M or less, more preferably about 0.1 M or less. Following renaturation, the resulting composition comprises substantially monomeric IFN-β, i.e., at least 51%, preferably at least 70% is in its monomeric form as determined, for example, using sizing HPLC, preferably using analytical ultracentrifugation (see, for example, Liu and Shire (1999) J. Pharm. Sci. 88:1237-1241, herein incorporated by reference). The residual guanidine HCl in this renatured IFN-β solution can be removed in a manner similar to that noted for the first purification method to prepare a pharmaceutical formulation comprising substantially monomeric IFN-β. Any pharmaceutically acceptable buffer may be utilized as noted elsewhere herein so long as the IFN-β remains solubilized and substantially in its monomeric form. In one embodiment, the pharmaceutically acceptable buffer is selected from the group consisting of glycine, aspartic acid, and sodium succinate, preferably glycine, such that the pharmaceutical formulation has a pH of about 3.0 to about 5.0, preferably about 3.0 to about 4.0, most preferably about 3.0.

Thus, the substantially monomeric form of IFN-β provided by the purification methods of the present invention has several uses as disclosed in the present invention. For example, this form of IFN-β can be used directly in formulating pharmaceutical compositions suitable for parenteral administration as noted herein. Following the diafiltration or dialysis step with a pharmaceutically acceptable buffer of choice to remove residual guanidine HCl, the resulting pharmaceutical compositions may be stabilized against denaturation and loss of biological activity by the inclusion of a stabilizer in the pharmaceutical compositions, which includes but is not limited to proteins or carbohydrates, preferably chosen from the group consisting of mannitol, sorbitol, glycerol, dextrose, sucrose, and trehalose, or a mixture thereof. In a further aspect of the present invention, the IFN-β preparation obtained from the diafiltration (or dialysis) and stabilization steps may be lyophilized and reconstituted in an inert, nontoxic, physiologically compatible carrier medium for therapeutic and clinical applications.

The pharmaceutical compositions of the invention are formulated with a known concentration of the substantially monomeric form of IFN-β such that administration of a particular dose promotes a desired therapeutic response with respect to a particular IFN-β responsive condition undergoing therapy. By "desired therapeutic response" is intended an improvement in the condition or in the symptoms associated with the condition.

Pharmaceutical compositions comprising the IFN-β are useful in therapy directed to treatment of IFN-β responsive conditions. By "therapy" is intended treatment of an existing normal condition that is enhanced by IFN-β therapy, therapeutic treatment of an abnormal condition that is responsive to IFN-β, and preventive or prophylactic procedures comprising treatment with IFN-β so as to prevent or lessen the severity of an occurrence of an abnormal condition. By "IFN-β-responsive condition" is intended any condition that responds either positively or negatively to IFN-β. Such an IFN-β-responsive condition may be a normal condition. For example, a mammal may undergo IFN-β therapy to increase the responsiveness and/or capability of the immune response. Such therapies encompass treatment to provide protection against or modulate the severity of viral infections, for example, Dengue virus or Sindbis virus. In contrast, the IFN-β-responsive condition may be an abnormal condition such as malignant melanoma. Such abnormal conditions may be chronic, and thus occur more or less continuously, or such abnormal conditions may be acute. The IFN-β-responsive condition might be a condition which could possibly be characterized as both chronic and acute, such as remitting-relapsing multiple sclerosis. Any IFN-β-responsive disorder may benefit from administration of the IFN-β pharmaceutical compositions of the present invention. Conditions responsive to IFN-β may also include immunological disorders, such as immunodeficiencies, including decreased immune tolerance as a result of disease or infection or damage to the immune response resulting from environmental or other effects, such as chemotherapy or other exposure to toxic chemicals.

The following examples are offered by way of illustration and not by way of limitation.

EXPERIMENTAL

EXAMPLE 1

Preparation of IFN-β

IFN-β for use in these experiments was produced in *E. coli* essentially as described in the first several steps of purification set forth in U.S. Pat. Nos. 4,462,940 and/or 4,816,400. That is, transformed bacteria were used to produce IFN-β; the host cells were concentrated, and their cell walls disrupted. The IFN-β was then prepared according to the methods of the present invention following preparation of a purified IFN-β pool.

The basic procedure was as follows:
1. Precipitate IFN-β from purified IFN-β pool using ethanol. Six parts of purified IFN-β pool are used for four parts of ethanol. This step yields more than 80% of the interferon as a pellet that can be centrifuged.
2. The pellet is then dissolved in 8 M guanidine HCl to a solution of about 10 mg/ml protein. This solubilization is rapid; the small amount of SDS present is not solubilized and is removed by filtration.
3. The resulting guanidine HCl solution is then diluted into a 10 mM buffer.

EXAMPLE 2

Dilution Parameters for Guanidine Hydrochloride Step

Figure 1:
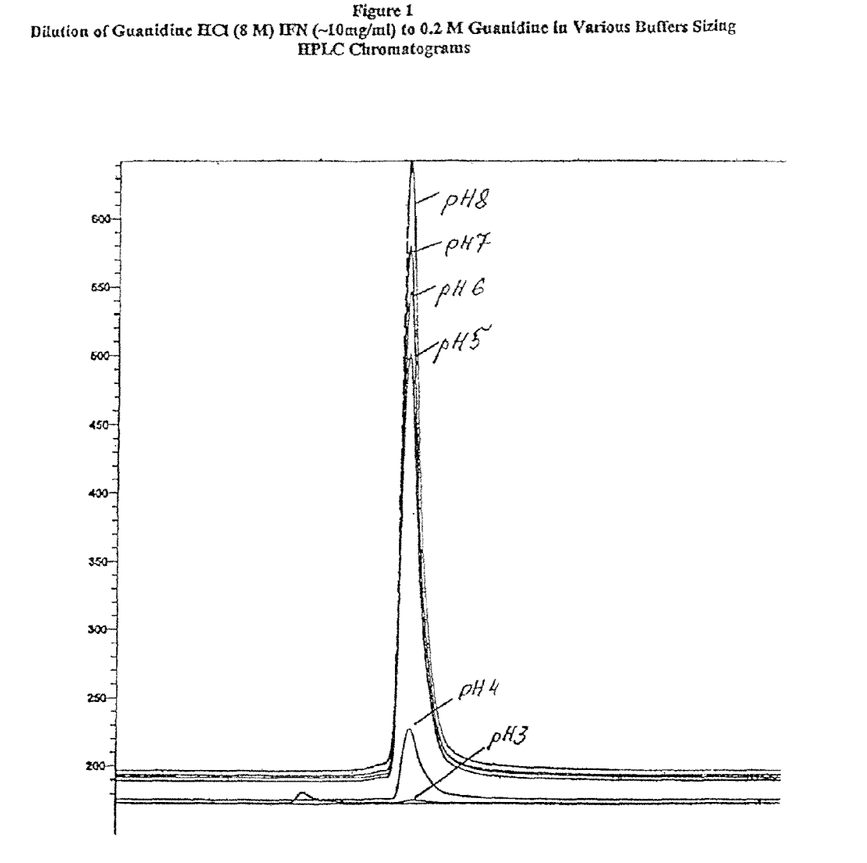
FIG. 1 shows sizing HPLC chromatography data collected following dilution of IFN-β from the guanidine hydrochloride solubilization step into various buffers.

Initial experiments were carried out to determine the optimal dilution parameters for the guanidine hydrochloride dilution step. A small-scale experiment that measured relative yields was carried out as outlined in Table 1; best results were obtained above pH 4.0 and below 0.8 M guanidine hydrochloride after dilution. The concentration of the interferon-beta monomer was determined using sizing HPLC with a 400 mM glycine pH 3.0 buffer. The results in Table 2 and a typical set of chromatograms in FIG. 1 show that although non-covalent multimers were obtained at lower pHs, monomeric interferon-beta was obtained at pH 5.0 and above.

TABLE 1

Relative Yield After Dilution of Guanidine HCl (8M)
IFN (~10 mg/ml) Estimated by HPLC

| | | Guanidine HCl Concentration After Dilution | | | |
|---|---|---|---|---|---|
| 10 mM Buffer | pH | 0.2M | 0.4M | 0.8M | 1.6M |
| Glycine | 3 | 2 | 2.1 | 1 | 1 |
| Sodium acetate | 4 | 13 | 12.7 | 6 | 2 |
| Sodium acetate | 5 | 68 | 68 | 33 | 30 |
| Sodium citrate | 6 | 79 | 62 | 43 | 42 |
| Sodium phosphate | 7 | 82 | 71 | 41 | 48 |
| Tris HCl | 8 | 99 | 83 | 40 | 38 |

TABLE 2

Percent Aggregates After Dilution of Guanidine HCl (8M)
IFN (~10 mg/ml) Determined by HPLC

| | | Guanidine HCl Concentration After Dilution | | | |
|---|---|---|---|---|---|
| 10 mM Buffer | pH | 0.2M | 0.4M | 0.8M | 1.6M |
| Glycine | 3 | 78 | 51 | 35 | 39 |
| Sodium acetate | 4 | <1 | 3 | 4 | 11 |
| Sodium acetate | 5 | 1 | 1 | 1 | 2 |
| Sodium citrate | 6 | 1 | 1 | 1 | 2 |
| Sodium phosphate | 7 | 1 | 1 | 1 | 3 |
| Tris HCl | 8 | 1 | 2 | 1 | 2 |

EXAMPLE 3

Yield of Guanidine Dilution Step

The process was scaled up to evaluate the yield of the guanidine dilution step. The results in Table 3 show that a 41% to 57% yield can be obtained with a forty-fold dilution at pH 6 to 8 with a final protein concentration of about 0.15 mg/ml. SDS concentrations in samples tested were less than 10 micrograms per milligram of IFN.

TABLE 3

Refolding Recovery from 8M Guanidine HCl (40× dilution)

| 10 mM Buffer | pH | [IFN] mg/ml | % Yield |
|---|---|---|---|
| Sodium citrate | 6 | 0.12 | 41 |
| Sodium phosphate | 7 | 0.17 | 57 |
| Tris HCl | 8 | 0.15 | 52 |

EXAMPLE 4

Removal of Residual Guanidine HCl Present After Dilution by Dialysis

Figure 2:
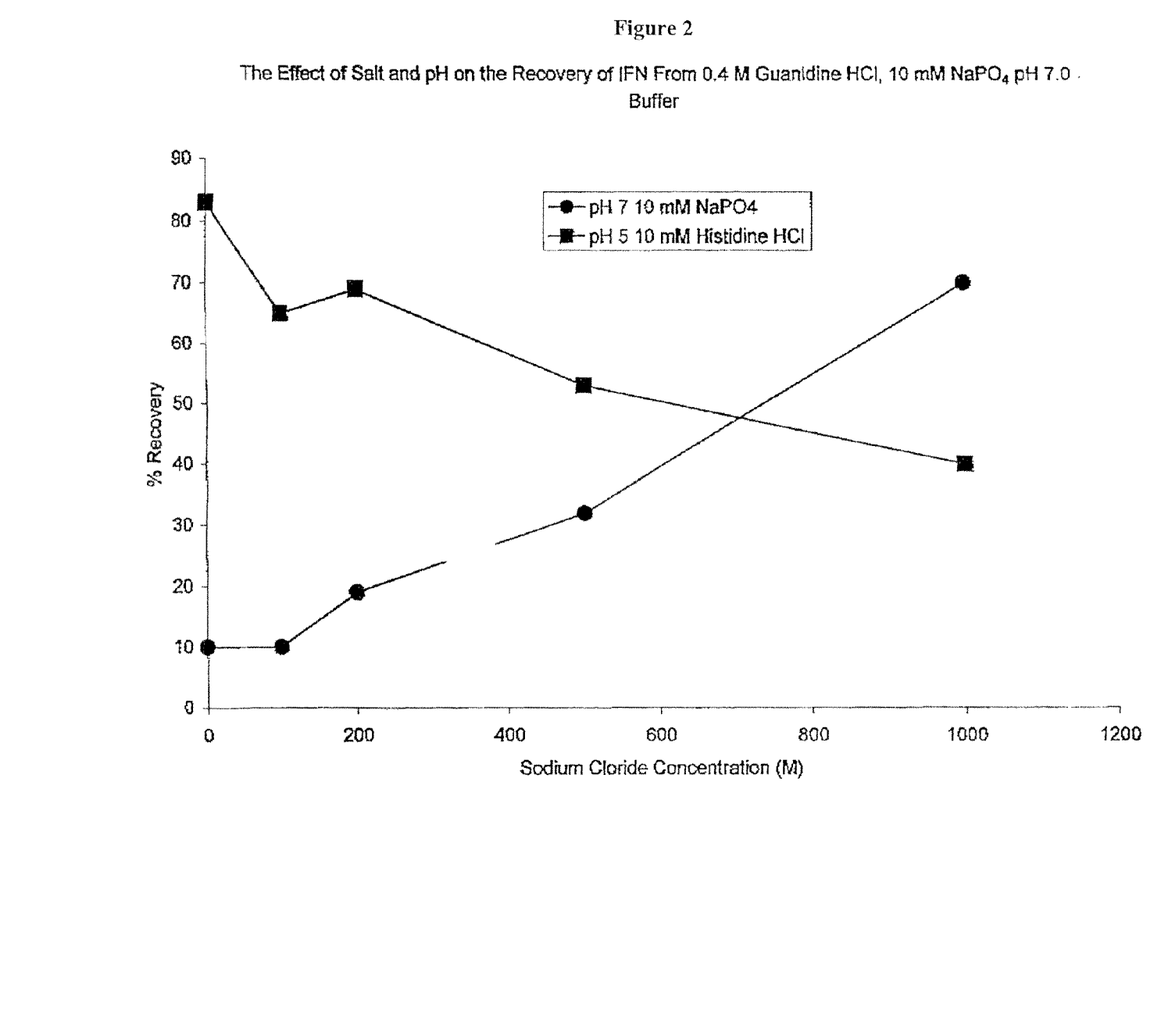
FIG. 2 shows the effect of salt and pH on the recovery of IFN-β from 0.4 M guanidine HCl, 10 mM NaPO4, pH 7.0 buffer.

Dialysis was used to remove residual guanidine HCl present after dilution. At pH 5, the highest yield, 83%, was obtained without additional NaCl present; and at pH 7.0, the highest yield, 70%, was obtained with 1000 mM NaCl present as shown in FIG. 2. In all cases, there was precipitation after dialysis, however the soluble fraction was monomeric, as assessed using sizing HPLC.

EXAMPLE 5

Effect of Agitation on Guanidine Hydrochloride-Renatured IFN-β Material

Figure 3:
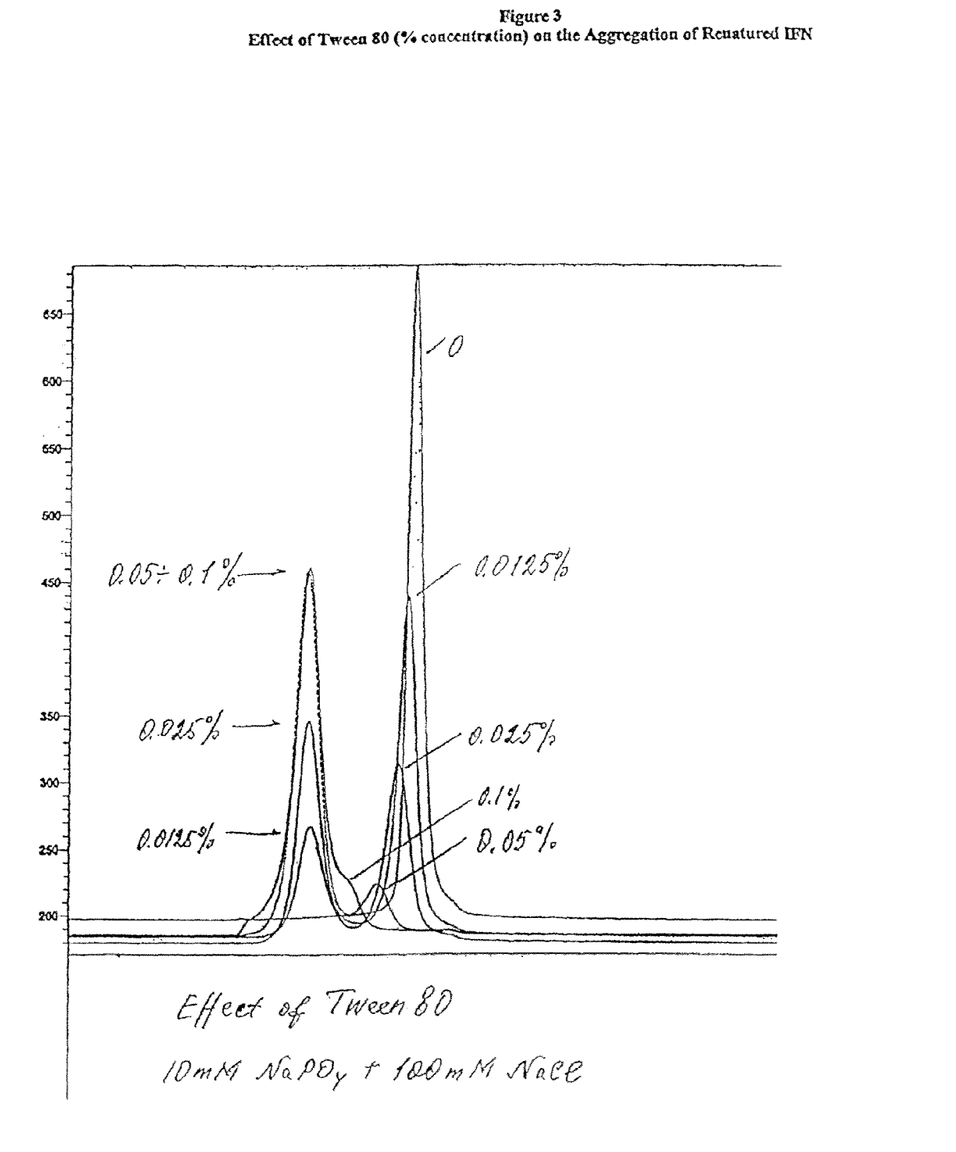
FIG. 3 shows the effect of Tween 80 on the aggregation of renatured IFN-β prepared according to the methods of the invention.

A small volume of IFN-β in buffer containing 10 mM phosphate (at pH 7.0) and 100 mM NaCl was placed in a tube on an end-over-end shaker. After about 3 hours, about 50% of the IFN-β material was precipitated. This suggests that stabilization will be enhanced by a suitable surfactant, such as Tween 80. The addition of Tween 80 stabilizes interferon and thereby increases the yield from the dialysis step. However, Tween 80 can also induce aggregation in a concentration-dependent manner, as shown in FIG. 3. These aggregates are soluble. Other surfactants may perform more optimally.

EXAMPLE 6

Protein Renaturation and Formulation Optimization by Using a Factorial Designed Approach A series of experiments were evaluated to estimate recovery of IFN-β during (1) denaturation of IFN-β in 8 M guanidine hydrochloride; (2) refolding of IFN-β by a rapid dilution with buffer; and (3) dialysis to remove residual guanidine hydrochloride with and without arginine present to obtain a final formulation. Composition of the formulation and conditions of steps 1-3 were optimized by using a half-factorial designed experiment. The factors used were protein concentration, guanidine hydrochloride concentration, pH, temperature, and arginine concentration.

It was found that pH, IFN-β concentration, guanidine hydrochloride concentration after dilution, and arginine concentration were significant model terms. The model's highest contributions were obtained from the IFN-β and arginine concentration. Interaction between arginine and pH played a significant role. The best results were obtained with 10 mM NaPO4 buffer pH 7.0 containing arginine in the final buffer. Total yield of steps 1-2 was up to 80-100% and yield of step 3 was 70-80%.

EXAMPLE 7

Removal of SDS and Formulation of IFN-β without the Use of Ethanol Precipitation Purified IFN-β-1b (1 L of 1.91 mg/ml in 0.4% SDS, 50 mM acetate buffer, pH 5.5) was stored at 5° C. During storage, some of the SDS present precipitated. 250 ml of this material (477.5 mg) was mixed with 229 g of guanidine hydrochloride (6 M, total volume 400 ml) and stirred at room temperature for 15 minutes using a magnetic stir bar. The 6 M guanidine hydrochloride/protein solution was then filtered with a Sartobran® P Capsule (0.45 μm pore size) to remove the precipitated SDS. The protein concentration as determined by UV at 280 nm was 1.02 mg/ml. The protein yield was 406 mg or 85%.

The 400 ml guanidine hydrochloride-treated material was concentrated utilizing a Millipore® Labscale® TFF diafiltration system (Millipore, Inc.) with two Pellicon® XL Biomax® 0.1 cm$^2$ 10 kD polysulfone membranes (Millipore, Inc.). The volume following the concentration step was 37 ml with a protein concentration of 10.3 mg/ml for a post-concentration yield of 381 mg or 93%.

Using a transfer pipette, 10 ml (103 mg) of the concentrated guanidine hydrochloride/protein solution were gradually added to 590 ml of 5 mM glycine, pH 3.2 solution. The buffer was at a rapid stir using a magnetic stir bar; the protein solution was added directly to the vortex. This 60× dilution of the 6 M guanidine hydrochloride/protein solution yielded a 0.1 M guanidine hydrochloride/protein solution at 0.17 mg/ml. This 600 ml was transferred to a 500 ml scale diafiltration unit equipped with two Pellicon® II 10 kD, 0.1 m$^2$ polysulfone membranes. This solution was initially concentrated to ~400 ml to a protein concentration of 0.23 mg/ml, and subsequently diafiltered against 9 volume changes (3.6 L) of 5 mM glycine at pH 3.2. The final diafiltrate (402 ml) was measured by UV at 280 nm for a final protein concentration of 0.23 mg/ml with a 92.46 mg or 90% yield for the diafiltration step, and an overall yield of 72% soluble protein for the purification process.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. Subheadings in the specification document are included solely for ease of review of the document and are not intended to be a limitation on the contents of the document in any way.

Although the foregoing invention has been described in some detail by way of illustration and example for purposes of clarity of understanding, it will be obvious that certain changes and modifications may be practiced within the scope of the invention.

That which is claimed is:

1. A method for preparing a formulation of interferon-beta (IFN-β), said method comprising:
   a) denaturing IFN-β with guanidine hydrochloride (HCl);
   b) renaturing the IFN-β via dilution into a first buffer to obtain a renatured IFN-β solution comprising residual guanidine HCl; and
   c) removing said residual guanidine HCl from said renatured IFN-β solution by diafiltration or dialysis of said renatured IFN-β solution into a second buffer that is pharmaceutically acceptable, wherein said second buffer is selected from the group consisting of aspartic acid and sodium succinate.

2. The method of claim 1, wherein said first buffer has a pH of about 3.0 to about 5.0, and wherein said residual guanidine HCl is present in said renatured IFN-β solution at a concentration of 1.6 M or less.

3. The method of claim 2, wherein said first buffer has a pH of about 3.0 to about 4.0, and wherein said residual guanidine HCl is present in said renatured IFN-β solution at a concentration of 0.2 M or less.

4. The method of claim 3, wherein said first buffer has a pH of about 3.0, and wherein said residual guanidine HCl is present in said renatured IFN-β solution at a concentration of 0.1 M or less.

5. The method of claim 1, wherein said IFN-β has the amino acid sequence set forth in SEQ ID NO:1 or SEQ ID NO:2.

6. The method of claim 1, wherein said IFN-β is glycosylated.

7. The method of claim 1, wherein said IFN-β is recombinantly produced.

8. The method of claim 1, wherein said IFN-β has at least 95% amino acid sequence identity with the amino acid sequence set forth in SEQ ID NO:1 as calculated using the ALIGN program (Version 2.0) with a PAM 120 weight residue table, a gap length penalty of 12, and a gap penalty of 4, and wherein said IFN-β retains the ability to bind to IFN-β receptors.

9. A method for preparing a composition comprising substantially monomeric interferon-beta (IFN-β) and having a pH of about 3.0 to about 5.0, said method comprising:
   a) preparing a precipitate of substantially purified INF-β;
   b) dissolving said precipitate in guanidine hydrochloride (HCl) to obtain a first solution comprising resolubilized denatured IFN-β; and
   c) renaturing said IFN-β by dilution of said first solution with a buffer, wherein said buffer has a pH of about 3.0 to about 5.0 and is selected from the group consisting of aspartic acid and sodium succinate.

10. The method of claim 9, wherein said IFN-β has the amino acid sequence set forth in SEQ ID NO:1 or SEQ ID NO:2.

11. The method of claim 9, wherein said IFN-β is glycosylated.

12. The method of claim 9, wherein said IFN-β is recombinantly produced.

13. The method of claim 9, wherein said IFN-β has at least 95% amino acid sequence identity with the amino acid sequence set forth in SEQ ID NO:1 as calculated using the ALIGN program (Version 2.0) with a PAM 120 weight residue table, a gap length penalty of 12, and a gap penalty of 4, and wherein said IFN-β retains the ability to bind to IFN-β receptors.

14. A method for preparing a formulation of interferon-beta (IFN-β, said method comprising:
   a) obtaining a sample comprising substantially purified IFN-β;
   b) mixing said sample with guanidine hydrochloride (HCl) to obtain a first solution comprising solubilized denatured IFN-β;
   c) diluting said first solution into a first buffer to obtain a second solution comprising solubilized renatured IFN-β and residual guanidine HCl; and
   d) removing residual guanidine HCl from said second solution by diafiltration or dialysis of said second solution into a second buffer that is pharmaceutically acceptable, wherein said second buffer is selected from the group consisting of aspartic acid and sodium succinate.

15. The method of claim 14, wherein said first buffer has a pH of about 3.0 to about 5.0, and wherein said residual guanidine HCl is present in said second solution at a concentration of 1.6 M or less.

16. The method of claim 15, wherein said first buffer has a pH of about 3.0 to about 4.0, and wherein said residual guanidine HCl is present in said second solution at a concentration of 0.2 M or less.

17. The method of claim 16, wherein said first buffer has a pH of about 3.0, and wherein said residual guanidine HCl is present in said renatured INF-β solution at a concentration of 0.1 M or less.

18. The method of claim 14, wherein said IFN-β has the amino acid sequence set forth in SEQ ID NO:1 or SEQ ID NO:2.

19. The method of claim 14, wherein said IFN-β is glycosylated.

20. The method of claim 14, wherein said IFN-β is recombinantly produced.

21. The method of claim 14, wherein said IFN-β has at least 95% amino acid sequence identity with the amino acid sequence set forth in SEQ ID NO:1 as calculated using the ALIGN program (Version 2.0) with a PAM 120 weight residue table, a gap length penalty of 12, and a gap penalty of 4, and wherein said IFN-β retains the ability to bind to IFN-β receptors.

22. A method for preparing a composition comprising substantially monomeric interferon-beta (IFN-β) and having a pH of about 3.0 to about 5.0, said method comprising:
   a) preparing a sample comprising substantially purified IFN-β;
   b) mixing said sample with guanidine hydrochloride (HCl) to obtain a first solution comprising solubilized denatured IFN-β; and
   c) renaturing said IFN-β by dilution of said first solution with a buffer, wherein said buffer has a pH of about 3.0 to about 5.0 and is selected from the group consisting of aspartic acid and sodium succinate.

23. The method of claim 22, wherein said buffer solution has a pH of about 3.0 to about 5.0.

24. The method of claim 22, wherein said IFN-β has the amino acid sequence set forth in SEQ ID NO:1 or SEQ ID NO:2.

25. The method of claim 22, wherein said IFN-β is glycosylated.

26. The method of claim 22, wherein said IFN-β is recombinantly produced.

27. The method of claim 22, wherein said IFN-β has at least 95% amino acid sequence identity with the amino acid sequence set forth in SEQ ID NO:1 as calculated using the ALIGN program (Version 2.0) with a PAM 120 weight residue table, a gap length penalty of 12, and a gap penalty of 4, and wherein said IFN-β retains the ability to bind to IFN-β receptors.

28. The method according to claim 1, wherein said composition comprises substantially monomeric IFN-β.

29. The method according to claim 14, wherein said composition comprises substantially monomeric IFN-β.

30. The method of claim 1, wherein said IFN-β composition is injectable.

31. The method of claim 14, wherein said INF-β composition is injectable.

32. The method of claim 1, wherein said INF-β is unglycosylated.

33. The method of claim 9, wherein said IFN-β is unglycosylated.

34. The method of claim 14, wherein said IFN-β is unglycosylated.

35. The method of claim 22, wherein said IFN-β is unglycosylated.

\* \* \* \* \*